(12) United States Patent
Cao et al.

(10) Patent No.: US 8,071,071 B2
(45) Date of Patent: Dec. 6, 2011

(54) TREATMENT OF SMALL PORE MOLECULAR SIEVES AND THEIR USE IN THE CONVERSION OF OXYGENATES TO OLEFINS

(75) Inventors: Guang Cao, Princeton, NJ (US); Gordon J. Kennedy, Washington, NJ (US); Matu J. Shah, Hackettstown, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 500 days.

(21) Appl. No.: 12/400,521

(22) Filed: Mar. 9, 2009

(65) Prior Publication Data

US 2009/0275789 A1 Nov. 5, 2009

Related U.S. Application Data

(60) Provisional application No. 61/050,102, filed on May 2, 2008.

(51) Int. Cl.
*C01B 39/00* (2006.01)
*C01B 39/02* (2006.01)
*C07C 1/20* (2006.01)

(52) U.S. Cl. ........... 423/700; 423/306; 585/640; 502/60

(58) Field of Classification Search .................. 423/700, 423/306
See application file for complete search history.

(56) References Cited

U.S. PATENT DOCUMENTS

| | | | |
|---|---|---|---|
| 3,030,181 A | 4/1962 | Milton | |
| 4,544,538 A | 10/1985 | Zones | |
| 5,206,195 A * | 4/1993 | Ando et al. | 502/64 |
| 5,900,226 A | 5/1999 | House | |
| 6,005,155 A * | 12/1999 | Sun | 585/640 |
| 6,709,644 B2 | 3/2004 | Zones et al. | |
| 7,008,612 B2 | 3/2006 | Corma Canós et al. | |
| 7,014,836 B2 | 3/2006 | Corma Canós et al. | |
| 7,056,489 B2 | 6/2006 | Corma Canós et al. | |
| 2003/0176751 A1 | 9/2003 | Strohmaier et al. | |
| 2005/0154244 A1 | 7/2005 | Cao et al. | |
| 2006/0115416 A1 | 6/2006 | Yuen | |
| 2006/0116541 A1 | 6/2006 | Yuen et al. | |
| 2007/0286798 A1 | 12/2007 | Cao et al. | |
| 2008/0045767 A1 | 2/2008 | Cao et al. | |

FOREIGN PATENT DOCUMENTS

| | | |
|---|---|---|
| EP | 0 500 413 | 9/1995 |
| FR | 2 540 093 | 3/1984 |
| GB | 868846 | 5/1961 |

(Continued)

OTHER PUBLICATIONS

Bordiga, et al., "Assessing the Acidity of High Silica Chabazite H-SSZ-13 by FTIR Using CO as Molecular Probe: Comparison with H-SAPO-34," Journal of Physical Chemistry B, (2005), 109, pp. 2779-2784.

(Continued)

*Primary Examiner* — David M Brunsman
(74) *Attorney, Agent, or Firm* — David M. Weisberg (57) ABSTRACT

A method is disclosed of treating a porous crystalline molecular sieve having a pore size less than or equal to about 5 Angstroms to decrease its coke selectivity in oxygenate to olefin conversion reactions. The method comprises contacting the molecular sieve with an acid having a kinetic diameter greater than or equal to that of acetic acid.

15 Claims, 2 Drawing Sheets

FOREIGN PATENT DOCUMENTS

| | | |
|---|---|---|
| WO | 93/24430 | 12/1993 |
| WO | WO 2005/040041 | 5/2005 |

OTHER PUBLICATIONS

Inui, et al., "Preparation of Silico-Alumino-Phosphates by the Rapid Crystallization Method and their Catalytic Performance in the Conversion of Methanol to Light Olefins," Applied Catalysis (1990), 58, 155-163.

Dahl et al., "Structural and Chemical Influences on the MTO Reaction: A Comparison of Chabazite and SAPO-34 as MTO Catalysts," Microporous and Mesoporous Materials (1999), 29, pp. 185-190.

Diaz-Cabañas et al., "Synthesis and Structure of Pure $SiO_2$ Chabazite: The $SiO_2$ Polymorph with the Lowest Framework Density," Chemical Communication 1881 (1998).

Hoffman, et al., "Synthesis of Hydrophobic Molecular Sieves by Hydrothermal Treatment with Acetic Acid," Chemtracts-Inorganic Chemistry, (2002), 15, pp. 455-459.

Jones, et al., "Synthesis of Hydrophobic Molecular Sieves by Hydrothermal Treatment with Acetic Acid," Chemistry of Materials (2001), 13, pp. 1041-1050.

Shao, et al., "Synthesis of Hydrothermally Stable and Long-Range Ordered Ce-MCM-48 and Fe-MCM-48 Materials," Journal of Physical Chemistry B, (2005), 109, pp. 20835-20841.

Garcia, et al., "Synthesis, Structure and Thermal Transformations of Aluminophosphates Containing the Nickel Complex [Ni(diethylenetriamine)$_2$]$^{2+}$ as a Structure Directing Agent," Microporous and Mesoporous Materials (2003), 58, pp. 91-104.

Barrer, et al., "The Hydrothermal Chemistry of the Silicates. Part VII: Synthetic Potassium Aluminosilicates," Journal of Chemical Society (1956), 562, pp. 2882-2891.

* cited by examiner

27Al MAS NMR Show No Framework Dealumination with Acetic Acid Treatment

FIG. 4

27Al MAS NMR Show Framework Dealumination with Formic and HCl Treatment, but not with Acetic Acid

TREATMENT OF SMALL PORE MOLECULAR SIEVES AND THEIR USE IN THE CONVERSION OF OXYGENATES TO OLEFINS

CROSS-REFERENCE TO RELATED APPLICATIONS

This application claims priority to U.S. Ser. No. 61/050,102, filed May 2, 2008, which is incorporated herein by reference.

FIELD OF THE INVENTION

This invention relates to a method of treating small pore size molecular sieves, particularly chabazite framework type molecular sieves, and to the use of the treated sieves in the conversion of oxygenates to olefins.

BACKGROUND OF THE INVENTION

The conversion of oxygenates to olefins (OTO) is currently the subject of intense research because it has the potential for replacing the long-standing steam cracking technology that is today the industry-standard for producing world scale quantities of ethylene and propylene. The very large volumes involved suggest that substantial economic incentives exist for alternate technologies that can deliver high throughputs of light olefins in a cost efficient manner. Whereas steam cracking relies on non-selective thermal reactions of naphtha range hydrocarbons at very high temperatures, OTO exploits catalytic and micro-architectural properties of acidic molecular sieves under milder temperature conditions to produce high yields of ethylene and propylene from methanol.

Current understanding of the OTO reactions suggests a complex sequence in which three major steps can be identified: (1) an induction period leading to the formation of an active carbon pool (alkyl-aromatics), (2) alkylation-dealkylation reactions of these active intermediates leading to products, and (3) a gradual build-up of condensed ring aromatics. OTO is therefore an inherently transient chemical transformation in which the catalyst is in a scontinuous state of change. The ability of the catalyst to maintain high olefin yields for prolonged periods of time relies on a delicate balance between the relative rates at which the above processes take place. The formation of coke-like molecules is of singular importance because their accumulation interferes with the desired reaction sequence in a number of ways. In particular, coke renders the carbon pool inactive, lowers the rates of diffusion of reactants and products, increases the potential for undesired secondary reactions and limits catalyst life.

Over the last two decades, many catalytic materials have been identified as being useful for carrying out the OTO reactions. Crystalline molecular sieves are the preferred catalysts today because they simultaneously address the acidity and morphological requirements for the reactions. Particularly preferred materials are small pore size (diameter less than or equal to about 5 Angstroms) molecular sieves, especially those having pores defined by eight-membered ring channel systems, such as those having the chabazite (CHA) framework type.

CHA framework type molecular sieves appear to be particularly suitable catalysts for the OTO reaction since they have cages that are sufficiently large to accommodate aromatic intermediates while still allowing the diffusional transport of reactants and products into and out of the crystals through regularly interconnected window apertures. By complementing such morphological characteristics with appropriate levels of acid strength and acid density, working catalysts are produced. Extensive research in this area indicates that in the case of CHA framework type aluminosilicates, increasing the silica to alumina molar ratio of the molecular sieve seems to be a key requirement in its use in OTO reactions.

Chabazite is a naturally occurring zeolite with the approximate formula $Ca_6Al_{12}Si_{24}O_{72}$. Three synthetic forms of chabazite are described in the following references: Zeolite K-G, described in "The Hydrothermal Chemistry of the Silicates. Part VII: Synthetic Potassium Aluminosilicates," J. Chem. Society (1956), pages 2882-2891, Barrer et al; Zeolite D, described in British Patent No. 868,846 (1961); and Zeolite R, described in U.S. Pat. No. 3,030,181 (1962). Zeolite K-G zeolite has a silica:alumina mole ratio of 2.3:1 to 4.15:1, whereas zeolites D and R have silica:alumina mole ratios of 4.5:1 to 4.9:1 and 3.45:1 to 3.65:1, respectively. The relatively low silica to alumina molar ratio of these materials makes them less than optimal as catalysts for OTO reactions.

Considerable work has therefore been conducted on the synthesis of CHA framework type aluminosilicate molecular sieves having high silica to alumina molar ratios and in particular with silica to alumina molar ratios greater than 15:1, preferably greater than 100:1.

For example, U.S. Pat. No. 4,544,538 describes the synthesis of a synthetic form of chabazite-type aluminosilicate, SSZ-13, using N-alkyl-3-quinuclidinol, N,N,N-tri-alkyl-1-adamantylammonium cations and/or N,N,N-trialkyl-exoaminonorbornane as a directing agent in a conventional $OH^-$ medium. According to the '538 patent, SSZ-13 typically has a silica to alumina molar ratio of 8 to 50 but it is stated that higher molar ratios can be obtained by varying the relative ratios of the reactants in the synthesis mixture and/or by treating the zeolite with chelating agents or acids to remove aluminum from the zeolite lattice. However, attempts to synthesize SSZ-13 in $OH^-$ media at silica to alumina molar ratios in excess of 100 have been unsuccessful and have produced ITQ-1 or SSZ-23, depending on the alkali metal cation present. Moreover, increasing the silica to alumina molar ratio of SSZ-13 by dealumination has met limited success.

U.S. Pat. No. 6,709,644 describes a zeolite that is identified as SSZ-62 and has a CHA framework-type and a crystal size of 0.5 micron or less. SSZ-62 is said to have a silica to alumina molar ratio in excess of 10, such as in excess of 30, but the only synthesis example produces a material with a silica to alumina molar ratio of 22. Synthesis is effected in a hydroxyl medium in the presence of N,N,N-trimethyl-1-adamantammonium cation as the structure directing agent. The zeolite can be steamed, purportedly to help stabilize the crystalline lattice to attack from acids.

An all silica crystalline molecular sieve having the CHA framework type has been hydrothermally synthesized using N,N,N-trimethyladamantylammonium in hydroxide form as the structure-directing agent, but the synthesis requires the presence of concentrated hydrofluoric acid. See Diaz-Cabanas, M-J, Barrett, P. A., and Camblor, M. A. "Synthesis and Structure of Pure $SiO_2$ Chabazite: the $SiO_2$ Polymorph with the Lowest Framework Density", Chem. Commun. 1881 (1998).

More recently, an aluminosilicate with the CHA framework type and having a silica to alumina molar ratio in excess of 100, such as from 150 to 2000, has been synthesized in the presence of fluoride ions. See U.S. Patent Application Publication No. 2003/0176751, published Sep. 18, 2003. Structure directing agents employed include N-alkyl-3-quinuclidinol, N,N,N-tri-alkyl-1-adamantammonium cations and N,N,N-trialkyl-exoaminonorbornane.

U.S. Published Patent Application No 2005/0154244, published Jul. 14, 2005, discloses a crystalline material comprising a CHA framework type molecular sieve with stacking faults or at least one intergrown phase of a CHA framework type molecular sieve and an AEI framework type molecular sieve, wherein the material is substantially free of framework phosphorus and has a composition involving the molar relationship (n)$X_2O_3$:$YO_2$ wherein X is a trivalent element, Y is a tetravalent element and n is from 0 to about 0.5. The material can be synthesized using a mixed directing agent comprising an N,N,N-trialkyl-1-adamantylammonium compound and an N,N-diethyl-2,6-dimethylpiperidinium compound, normally in the presence of fluoride ions.

U.S. Published Patent Application No 2006/0115416, published Jun. 1, 2006, discloses a fluoride-free synthesis method for preparing a molecular sieve having the CHA crystal structure and a silica to alumina mole ratio of greater than 50:1, the method comprising: (a) forming an aqueous reaction mixture comprising a composition in terms of mole ratios falling within the following ranges:

$YO_2/W_aO_b$ 220-∞
$OH^-/YO_2$ 0.19-0.52
$Q/YO_2$ 0.15-0.25
$M_{2/n}O/YO_2$ 0.04-0.10
$H_2O/YO_2$ 10-50 wherein Y is silicon, germanium or mixtures thereof, W is aluminum, iron, titanium, gallium or mixtures thereof, a is 1 or 2, b is 2 when a is 1 or b is 3 when a is 2; M is an alkali metal or alkaline earth metal, n is the valence of M, and Q is a cation derived from 1-adamantamine, 3-quinuclidinol or 2-exo-aminonorbornane; and (b) maintaining said aqueous mixture under sufficient crystallization conditions until crystals are formed.

U.S. Published Patent Application No 2008/0045767, published Feb. 21, 2008, discloses a method of synthesizing a crystalline material comprising a CHA framework type molecular sieve and having a composition involving the molar relationship:

$(n)X_2O_3$:$YO_2$ wherein X is a trivalent element; Y is a tetravalent element; and n is from 0 to less than 0.01, such as from about 0.0005 to about 0.007, the method comprising:

(a) preparing a reaction mixture capable of forming said material, said mixture comprising a source of water, a source of an oxide of a tetravalent element Y and optionally a source of an oxide of a trivalent element X, wherein the reaction mixture is substantially free of fluoride ions added as HF and further comprises an organic directing agent having the formula:

$[R^1R^2R^3N-R^4]^+Q^-$ wherein $R^1$ and $R^2$ are independently selected from hydrocarbyl alkyl groups and hydroxy-substituted hydrocarbyl groups having from 1 to 3 carbon atoms, provided that $R^1$ and $R^2$ may be joined to form a nitrogen-containing heterocyclic structure, $R^3$ is an alkyl group having 2 to 4 carbon atoms and $R^4$ is selected from a 4- to 8-membered cycloalkyl group, optionally substituted by 1 to 3 alkyl groups each having from 1 to 3 carbon atoms, and a 4- to 8-membered heterocyclic group having from 1 to 3 heteroatoms, said heterocyclic group being optionally substituted by 1 to 3 alkyl groups each having from 1 to 3 carbon atoms and the or each heteroatom in said heterocyclic group being selected from the group consisting of O, N, and S, or $R^3$ and $R^4$ are hydrocarbyl groups having from 1 to 3 carbon atoms joined to form a nitrogen-containing heterocyclic structure; and $Q^-$ is an anion;

(b) maintaining said reaction mixture under conditions sufficient to form crystals of said crystalline material; and (c) recovering said crystalline material.

Because of the hazards inherent in working with HF, synthesis routes that will produce molecular sieves without the addition of fluoride ions are preferred. However, in the case of high silica CHA framework type materials, many of the synthesis routes that operate in the absence of HF produce molecular sieves that exhibit reduced OTO performance and particularly a high selectivity to coke as compared with the desired olefin products. There is significant interest in developing post-treatment methods for improving the OTO performance of CHA framework type and other small pore molecular sieves.

According to the present invention, it has now been found that the OTO performance of small pore size molecular sieves, such as high silica CHA framework type molecular sieves, and especially those produced by fluoride fee syntheses, can be enhanced by treatment with acids, particularly acetic acid, having a larger kinetic diameter than the pore diameter of the molecular sieve. In particular, it is found that the selectivity of the molecular sieves to undesirable coke and propane is reduced by the acid treatment, while the selectivity to ethylene and propylene is enhanced or substantially unaffected by the treatment. The desirable result is unexpected because NMR analysis suggests that there is no change in defect concentration or framework aluminum content as a result of the treatment. However, the improvement is significant and reproducible, indicating that the acid treatment is a promising method for improving the catalytic performance of fluoride-free high silica CHA materials. In contrast, it is found that treatment with acids, such as formic and hydrochloric acid, having a smaller kinetic diameter than acetic acid seems to lead to loss of crystallinity and reduced selectivity to ethylene and propylene.

In our co-pending United States Patent Application Publication No. 2007/0286798, published Dec. 13, 2007, we have described a process for improving the OTO performance of high silica CHA framework type molecular sieves, including those produced by fluoride free synthesis, by treating the molecular sieve with an atmosphere containing steam at a temperature of about 400° C. to about 650° C. for a time of about 8 hours to about 170 hours. The steaming is said to heal defects in the framework structure of the molecular sieve and to improve OTO performance by increasing the prime olefin selectivity of the molecular sieve.

Acetic acid treatment has been reported to heal framework defects in large pore (12-ring) molecular sieves. See, for example, Jones et al. "Synthesis of Hydrophobic Molecular Sieves by Hydrothermal Treatment with Acetic Acid", Chemistry of Materials (2001), 13(3), pages 1041-1050. However, given the proposed mechanism in this article for the acetic acid treatment (dissolution of silica and transport of monomeric silicic acid-like species through the porous interior for insertion at the defect sites), similar results would not be expected with small pore zeolites, since the 8-ring pore opening is too small to allow silicic acid to be mobile within the pore system. In fact, no reports have been found of the use of acetic acid to treat small pore (8-ring) zeolites, such as CHA framework type materials.

SUMMARY OF THE INVENTION

In one aspect, the invention resides in a method of treating a porous crystalline molecular sieve having a pore size less than or equal to about 5 Angstroms, the method comprising contacting said molecular sieve with an acid having a kinetic diameter greater than the pore diameter of the molecular sieve.

Conveniently, molecular sieve has pores defined by an eight-membered ring channel system and especially comprises a CHA framework type material.

In one embodiment, the molecular sieve has a composition substantially free of framework phosphorus and involving the molar relationship:

$$(n)X_2O_3{:}YO_2,$$

wherein X is a trivalent element, Y is a tetravalent element, and n is non-zero and less than 0.07, such as non-zero and less than 0.02, for example non-zero and less than 0.01. Generally, Y is silicon, tin, titanium germanium or a combination thereof, especially, silicon, and X is aluminum, boron, iron, indium, gallium or a combination thereof, especially aluminum.

In one embodiment, the molecular sieve, in its as-synthesized form, is substantially free of fluoride ions.

Conveniently, the acid is selected from acetic acid, propionic acid, oxalic acid, citric acid, tartaric acid, benzoic acid, phthalic acid, and combinations thereof, and especially contains acetic acid.

Conveniently, the contacting is conducted at a temperature of about 50° C. to about 300° C. for a time of about 0.1 hours to about 240 hours.

Conveniently, the acid employed in said contacting is present as a 0.01 Molar to 10 Molar aqueous solution.

In a further aspect, the invention resides in a method of treating a porous crystalline molecular sieve comprising a CHA framework type material, the method comprising contacting said molecular sieve with acetic acid.

In yet a further aspect, the invention resides in the use of the treated molecular sieve described herein in a process for converting organic oxygenate compounds to olefins.

DETAILED DESCRIPTION OF THE EMBODIMENTS

Described herein is a method of treating a small pore size (diameter less than or equal to about 5 Angstroms) molecular sieve, especially a molecular sieve comprising a CHA framework type material, by contacting the molecular sieve with an acid having a kinetic diameter greater than the pore diameter of the molecular sieve. The treated molecular sieve is found to have decreased selectivity to unwanted coke and propane when used as a catalyst in the conversion of organic oxygenates to olefins, especially ethylene and propylene.

The present method can be employed with any molecular sieve having a pore size less than or equal to about 5 Angstroms, although it is especially applicable to molecular sieves having at least one set of pores defined by an eight-membered ring channel system. In this respect, it will be understood that the pores of many molecular sieves are not circular in cross-section and hence references herein to "pore size" of a molecular sieve are intended to mean the average cross sectional dimension of the pores of the molecular sieve.

Molecular sieves are classified by the Structure Commission of the International Zeolite Association according to the rules of the IUPAC Commission on Zeolite Nomenclature. According to this classification, framework-type zeolites and other crystalline microporous molecular sieves, for which a structure has been established, are assigned a three letter code and are described in the Atlas of Zeolite Framework Types, 6th Revised Edition, Elsevier, (2007). Examples of suitable small pore molecular sieves for use in the present method include those having at least one of the structure types selected from AEI, CHA, ERI, LEV, AFX, LTA, ITE, DDR, and KFI, as well as substituted and intergrown forms thereof.

In particular, the present method is useful in the treatment of small pore size molecular sieves substantially free of framework phosphorus and especially those having a composition involving the molar relationship:

$$(n)X_2O_3{:}YO_2,$$

wherein X is a trivalent element, Y is a tetravalent element, and n is less than 0.07, such as less than 0.02, for example less than 0.01. In a preferred embodiment, n is also non-zero, such as at least 0.0001, for example at least 0.0003, at least 0.0005, at least 0.0007, at least 0.001, at least 0.0015, at least 0.002, or at least 0.025. Generally, Y is silicon, tin, titanium germanium or a combination thereof, especially, silicon, and X is aluminum, boron, iron, indium, gallium or a combination thereof, especially aluminum.

In one practical embodiment, the molecular sieve employed in the present method is a CHA-containing molecular sieve having the composition described above, particularly a silicate or aluminosilicate, wherein the molecular sieve has been synthesized from a fluoride-free reaction mixture. One example of such a fluorine-free synthesis of a CHA-containing molecular sieve is disclosed in U.S. Published Patent Application No 2008/0045767, the entire content of which is incorporated herein by reference. In this synthesis process the CHA-containing molecular sieve is crystallized from a reaction mixture including a structure directing agent having the general formula:

$$[R^1R^2R^3N{-\!\!\!-}R^4]^+Q^-$$

wherein $R^1$ and $R^2$ are independently selected from hydrocarbyl alkyl groups and hydroxy-substituted hydrocarbyl groups having from 1 to 3 carbon atoms, provided that $R^1$ and $R^2$ may be joined to form a nitrogen-containing heterocyclic structure, $R^3$ is an alkyl group having 2 to 4 carbon atoms and $R^4$ is selected from a 4- to 8-membered cycloalkyl group, optionally substituted by 1 to 3 alkyl groups each having from 1 to 3 carbon atoms, and a 4- to 8-membered heterocyclic group having from 1 to 3 heteroatoms, said heterocyclic group being optionally substituted by 1 to 3 alkyl groups each having from 1 to 3 carbon atoms and the or each heteroatom in said heterocyclic group being selected from the group consisting of O, N, and S, or $R^3$ and $R^4$ are hydrocarbyl groups having from 1 to 3 carbon atoms joined to form a nitrogen-containing heterocyclic structure; and $Q^-$ is a anion. Suitable structure directing agent include N,N,N-dimethylethylcyclohexylammonium, N,N,N-methyldiethylcyclohexylammonium, and N,N,N-triethylcyclohexylammonium cations.

In the present treatment method, the small pore molecular sieve is contacted with an acid, especially an organic acid, such as a carboxylic acid, having a kinetic diameter that is comparable to or larger than the pore diameter of the molecular sieve. In this respect, the kinetic diameter of any given molecule is the diameter of the imaginary cylinder that can circumscribe the molecule in its most favorable equilibrium conformation. The kinetic diameter of any organic molecule can readily be calculated from the dimensions and configuration of its constituent atoms using commonly available molecular mechanics computational software. By employing an acid having a kinetic diameter greater than that of acetic acid, the acid is essentially constrained from entering the pores of the molecular sieve during the treatment process. Suitable acids for use in the present treatment method can include, but are not limited to, acetic acid, propionic acid, oxalic acid, citric acid, tartaric acid, benzoic acid, phthalic acid, and combinations thereof, and especially includes acetic acid.

The conditions employed in the present treatment process are not closely controlled but generally include a temperature from about 50° C. to about 300° C., such as about 100° C. to about 250° C. for a time of about 0.1 hours to about 240 hours, such as about 1 hour to about 96 hours. The treatment process can be conducted on the as-synthesized molecular sieve (containing the directing agent employed to direct its synthesis) or on the molecular sieve after calcination or other treatment to remove the structure directing agent, or after cation exchange to remove the alkaline metal ions.

The molecular sieve treated in accordance with the present method can be particularly useful as a catalyst in the conversion of organic oxygenate compounds to olefins, especially ethylene and propylene.

As used herein, the term "organic oxygenate compounds" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety will normally contain from about 1 to about 10 carbon atoms, such as from about 1 to about 4 carbon atoms.

Representative organic oxygenate compounds include lower straight chain or branched aliphatic alcohols, their unsaturated counterparts, and their nitrogen, halogen and sulfur analogues. Examples of suitable oxygenate compounds include methanol; ethanol; n-propanol; isopropanol; $C_4$ to $C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol. As used herein, the term "organic oxygenate compound" designates only the organic material used as the feed. The total charge of feed to the reaction zone may contain additional compounds, such as diluents.

In such an oxygenate conversion process, a feedstock comprising an organic oxygenate compound, optionally with one or more diluents, is contacted in the vapor phase in a reaction zone with a catalyst comprising the present molecular sieve at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is(are) generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example from about 250° C. to about 800° C., including from about 250° C. to about 750° C., conveniently from about 300° C. to about 650° C., typically from about 350° C. to about 600° C. and particularly from about 400° C. to about 600° C.

Light olefin products will form, although not necessarily in optimum amounts, at a wide range of pressures, including but not limited to autogenous pressures and pressures in the range from about 0.1 kPa to about 10 MPa. Conveniently, the pressure is in the range of from about 7 kPa to about 5 MPa, such as in the range of from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

A wide range of weight hourly space velocities (WHSV) for the feedstock will function in the oxygenate conversion process. WHSV is defined as weight of feed (excluding diluent) per hour per weight of a total reaction volume of molecular sieve catalyst (excluding inerts and/or fillers). The WHSV generally should be in the range from about 0.01 $hr^{-1}$ to about 500 $hr^{-1}$, such as in the range of from about 0.5 $hr^{-1}$ to about 300 $hr^{-1}$, for example in the range of from about 0.1 $hr^{-1}$ to about 200 $hr^{-1}$.

A practical embodiment of a reactor system for the oxygenate conversion process is a circulating fluid bed reactor with continuous regeneration, similar to a modern fluid catalytic cracker. Fixed beds are generally not preferred for the process because oxygenate to olefin conversion is a highly exothermic process which requires several stages with intercoolers or other cooling devices. The reaction also results in a high pressure drop due to the production of low pressure, low density gas.

When used as a catalyst in the conversion of organic oxygenate compounds to olefins, the molecular sieve treated by the present method is found to exhibit reduced selectivity to coke and normally reduced selectivity to propane as compared with the untreated molecular sieve. In this respect, the treated molecular sieve often also exhibits enhanced oxygenate conversion activity as compared with the untreated molecular sieve so that the absolute amount of methanol converted and coke produced in a given reaction time may exceed that obtained with the untreated molecular sieve. However, the coke selectivity, that is the amount of coke produced by weight of the oxygenate converted, is less for the treated molecular sieve than the untreated material.

Additionally or alternately, the invention can be further described by the following embodiments.

Embodiment 1

A method of treating a porous crystalline molecular sieve having a pore size less than or equal to 5 Angstroms, the method comprising contacting said molecular sieve with an acid having a kinetic diameter greater than or equal to that of acetic acid.

Embodiment 2

A method of treating a porous crystalline molecular sieve comprising a CHA framework type material, the method comprising contacting said molecular sieve with acetic acid.

Embodiment 3

The method of any of embodiments 1-2, wherein said molecular sieve has pores defined by an eight-membered ring channel system.

Embodiment 4

The method of embodiment 1 or embodiment 3, wherein said molecular sieve comprises a CHA framework type material.

Embodiment 5

The method of any of embodiments 1 and 3-4, wherein said acid is selected from acetic acid, propionic acid, oxalic acid, citric acid, tartaric acid, benzoic acid, phthalic acid, and combinations thereof, or preferably contains acetic acid.

Embodiment 6

The method of any of the previous embodiments, wherein said contacting is conducted at a temperature of about 50° C. to about 300° C. for a time of about 0.1 hours to about 240 hours.

Embodiment 7

The method of any of embodiments 2 and 5-6, wherein said acetic acid employed in said contacting is present as a 0.01 Molar to 10 Molar aqueous solution.

Embodiment 8

The method of any of the previous embodiments, wherein the molecular sieve, in its as-synthesized form, is substantially free of fluoride ions.

Embodiment 9

The method of any of the previous embodiments, wherein said molecular sieve has a composition substantially free of framework phosphorus and involving the molar relationship: $(n)X_2O_3:YO_2$, wherein X is a trivalent element, Y is a tetravalent element, and n is non-zero and less than 0.07, for example less than 0.02 or less than 0.01.

Embodiment 10

The method of embodiment 9, wherein Y is silicon, tin, titanium, germanium, or a combination thereof, preferably silicon.

Embodiment 11

The method of embodiment 9, wherein n is at least 0.0005 and X is aluminum, boron, iron, indium, gallium, or a combination thereof, preferably aluminum.

Embodiment 12

The method of any of the previous embodiments, wherein said treated molecular sieve, when used to convert a methanol-containing feed to olefins, produces less coke by weight of methanol converted as compared with the untreated molecular sieve when used to convert the same methanol-containing feed under identical conditions.

Embodiment 13

A crystalline material comprising a CHA framework type molecular sieve treated by the method of any of the previous embodiments.

Embodiment 14

A process for producing olefins comprising contacting an organic oxygenate compound under oxygenate conversion conditions with a catalyst comprising the crystalline material of embodiment 13.

Embodiment 15

The process of embodiment 14, wherein said treated CHA framework type molecular sieve produces less coke by weight of organic oxygenate compound converted than the untreated CHA framework type molecular sieve when each is contacted with said organic oxygenate compound under identical oxygenate conversion conditions.

The invention will now be more particularly described with reference to the Examples and the accompanying drawings.

Examples 1 to 5

Synthesis of F-Free High Silica Chabazite

The following ingredients were mixed, in sequence, and blended into a uniform gel: about 50 wt % NaOH, 42.7 wt % N,N,N-dimethylethylcyclohexylammonium hydroxide (DMECHA$^+$OH$^-$) solution, deionized water if necessary, Hi-Sil® 233 (PPG Industries, USA) containing about 0.53 wt % Na, about 0.01 wt % K, about 0.42 wt % alumina, and about 82.2 wt % silica, and Catapal™ A (CONDEA Vista Company, Texas, USA) which contained about 71.5 wt % $Al_2O_3$. About 200 ppm colloidal seeds having the LEV structure were added lastly. Five separate mixtures were made that had the following molar compositions:

0.091NaOH:0.182DMECHA$^+$OH$^-$:xAl$_2$O$_3$:1.00 SiO$_2$: 6.36H$_2$O, where x=~0.017, ~0.010 (two samples), ~0.0063, and ~0.0036

The mixtures were individually sealed in Teflon-lined Parr autoclaves and heated in a ~160° C. oven for about 72 hours, while the autoclaves were tumbled at about 40 rpm. The autoclaves were cooled to room temperature. The contents were centrifuged and the solid was washed repeatedly with deionized water. The solid product was dried in a vacuum oven at about 50° C. X-ray powder diffraction was used for phase identification, which confirmed that all solid products were chabazite without detectable impurities.

The products were calcined in a muffle furnace with the following protocol: under flowing nitrogen, ramp to about 400° C. at about 10° C./min, then dwell at about 400° C. for about 30 minutes, after switching to flowing air, ramp at about 10° C./min to about 650° C., dwell at about 650° C. for about 4 hours and then cool approximately to room temperature. The calcined samples were ion-exchanged three times with about 5 wt % ammonium sulfate solution, and washed with deionized water until the electrical conductivity of the supernatant was lower than about 50 mS/cm.

Elemental analysis of the calcined/$NH_4$-exchanged/dried samples was performed using Inductively Coupled Plasma Spectroscopy (ICP). The results are shown below in Table 1.

TABLE 1

| | Example | | | | |
|---|---|---|---|---|---|
| | 1 | 2 | 3 | 4 | 5 |
| x ($Al_2O_3/SiO_2$ ratio) in Gel | 0.017 | 0.010 | 0.010 | 0.0063 | 0.0036 |
| Si/Al ratio of gel mixture | 30.0 | 50.0 | 50.0 | 80.0 | 140 |
| Si/Al ratio of $NH_4$-exchanged samples | 26.7 | 51.8 | 53.8 | 73.5 | 118 |
| Si/Al ratio of acetic acid treated samples | 26.7 | 52.5 | | | |
| Na/Al ratio of $NH_4$-exchanged samples | 0.02 | 0.04 | 0.01 | 0.05 | 0.11 |

Example 6

Acetic Acid Treatment

About 0.54 g each of the $NH_4$-exchanged samples above was heated to about 200° C. in a muffle furnace under flowing nitrogen for about 30 minutes. The powder was then suspended in a solution of about 4.0 g glacial acetic acid and about 10.0 g deionized water. The mixture was sealed in a ~23-mL Teflon-lined Parr autoclave and was heated to about 180° C. for about 7 days. The resultant solid was recovered by centrifugation and washed with deionized water, and was then dried in a ~50° C. oven. Some of the samples were subjected to the acetic acid treatment twice (designated as 2× as opposed to 1× for one-time treatment in Table 2).

Example 7

Methanol-to-Olefins Performance Test

Each of the untreated chabazite samples of Examples 1 to 5 and the acetic acid treated samples of Example 6 were subjected to testing in the methanol-to-olefins (MTO) reaction in a fixed-bed microreactor. Methanol was fed at a preset pressure and rate to a reactor tube (made of stainless steel) that was housed in an isothermally heated zone. The reactor tube contained about 20 mg weighed and sized granules of the catalyst sample (20-40 mesh by the press-and-screen method). The catalyst was activated for about 30 minutes at about 500° C. in flowing nitrogen before methanol was admitted. The MTO testing was conducted at a reactor temperature of about 540° C., a methanol pressure of about 40 psia (about 276 kPa) and a methanol weight hourly space velocity (WHSV) of about 100 $hr^{-1}$.

The product effluent was sampled, at different times during the run, with a twelve-port sampling loop while the catalyst was continuously deactivating. The effluent sample in each port was analyzed with a Gas Chromatograph equipped with an FID detector. The amount of coke on the catalysts at the end of the MTO test was determined by passing $O_2$ in helium over the coked catalyst and measuring the amount of CO and $CO_2$ evolved during a temperature ramp up to 800° C. (Temperature Programmed Oxidation, or TPO). Cumulative conversion of methanol was expressed as grams of methanol converted per gram of sieve catalyst (CMCPS). On-stream lifetime refers to the CMCPS when methanol conversion has dropped to 10%. The product selectivity is reported as the average over the entire conversion range, rather than from a single point in effluent composition. The results are shown in Table 2.

TABLE 2

| Example | Coke wt % on sieve | Coke select. % MeOH | Total g MeOH conv. | $C_2^=+C_3^=$ | $C_2^=/C_3^=$ | $C_4^+$ | $CH_4$ | $C_2^=$ | $C_2H_6$ | $C_3^=$ | $C_3H_8$ | $C_4$'s | $C_5$'s | $C_6+$'s |
|---|---|---|---|---|---|---|---|---|---|---|---|---|---|---|
| Ex 1 - untreated | 18.6 | 3.52 | 5.29 | 66.7 | 1.30 | 14.7 | 4.89 | 37.7 | 1.90 | 29.0 | 3.54 | 11.4 | 2.75 | 0.52 |
| Ex 1 - acetic treated 1× | 21.2 | 2.90 | 7.34 | 1.35 | 1.35 | 13.9 | 5.56 | 39.5 | 2.07 | 29.2 | 2.82 | 11.2 | 2.33 | 0.35 |
| Ex 2 - untreated | 22.7 | 2.68 | 8.47 | 71.7 | 1.60 | 10.7 | 8.88 | 44.1 | 1.11 | 27.6 | 1.06 | 8.4 | 1.97 | 0.33 |
| Ex 2 - acetic treated 1× | 25.5 | 2.33 | 10.94 | 73.7 | 1.65 | 10.9 | 7.67 | 45.9 | 1.09 | 27.8 | 0.96 | 8.7 | 1.88 | 0.33 |
| Ex 2 - acetic treated 2× | 25.2 | 2.15 | 11.73 | 71.7 | 1.48 | 12.3 | 8.81 | 42.8 | 1.07 | 28.9 | 0.83 | 9.7 | 2.25 | 0.39 |
| Ex 3 - untreated | 18.5 | 2.13 | 8.70 | 72.1 | 1.67 | 11.5 | 8.13 | 45.0 | 1.33 | 27.0 | 1.52 | 8.8 | 2.32 | 0.41 |
| Ex 3 - acetic treated 1× | 21.2 | 2.08 | 10.19 | 70.5 | 1.37 | 13.6 | 9.01 | 40.8 | 0.96 | 29.7 | 0.68 | 10.8 | 2.38 | 0.41 |
| Ex 4 - untreated | 17.9 | 1.81 | 9.86 | 69.2 | 1.28 | 15.1 | 9.47 | 38.8 | 0.88 | 30.3 | 0.64 | 11.7 | 2.86 | 0.52 |
| Ex 4 - acetic treated 1× | 19.5 | 1.58 | 12.36 | 72.1 | 1.39 | 14.3 | 8.17 | 41.9 | 0.83 | 30.2 | 0.59 | 11.2 | 2.60 | 0.46 |
| Ex 5 - untreated | 12.0 | 1.59 | 7.56 | 69.3 | 1.14 | 17.9 | 7.58 | 36.9 | 0.65 | 32.4 | 0.41 | 13.9 | 3.39 | 0.68 |
| Ex 5 - acetic treated 1× | 8.4 | 0.89 | 9.45 | 70.9 | 1.11 | 20.1 | 5.78 | 37.3 | 0.47 | 33.6 | 0.27 | 15.6 | 3.77 | 0.79 |
| Ex 5 - acetic treated 2× | 5.1 | 0.70 | 7.33 | 71.7 | 1.10 | 20.4 | 5.17 | 37.5 | 0.44 | 34.2 | 0.28 | 15.9 | 3.80 | 0.70 |

($C_n^=$ denotes an olefin with n carbon atoms)

The data in Table 2 show that in all cases acetic acid treatment resulted in a reduction in both coke selectivity and propane (denoted as $C_3H_8$) selectivity. It is to be noted that reductions in propane and coke selectivity are usually associated with reduction of acid site density, i.e., increase in Si/Al ratio. In this case, however, no evidence of dealumination or change in Si/Al ratio was found.

Example 8

Formic Acid and Hydrochloric Acid Treatment

Part of the untreated product of Example 2 was separately treated with about 13-14 mL of formic acid and HCl solutions. The solution of formic acid was prepared by addition of about 3.07 g formic acid to about 10.0 g deionized water, whereas the HCl solution was prepared by addition of about 2.5 g ~37% HCl to about 497.5 g deionized water. The pH of the acid solutions was targeted to be the same, measured at between about 1 and about 2. The temperature and time of the treatment was the same as the acetic-acid treatment: about 180° C. and about 7 days. The compositions of the samples before and after the treatments were determined by ICP and the results are listed in Table 3.

TABLE 3

|  | $NH_4$-Chabazite | Acetic Acid Treated | Formic Acid Treated | HCl Treated |
|---|---|---|---|---|
| Si/Al Ratio | 51.8 | 52.5 | 51.3 | 49.3 |
| Na/Al Ratio | 0.04 | 0.02 | 0.02 | 0.02 |

Figure 1:
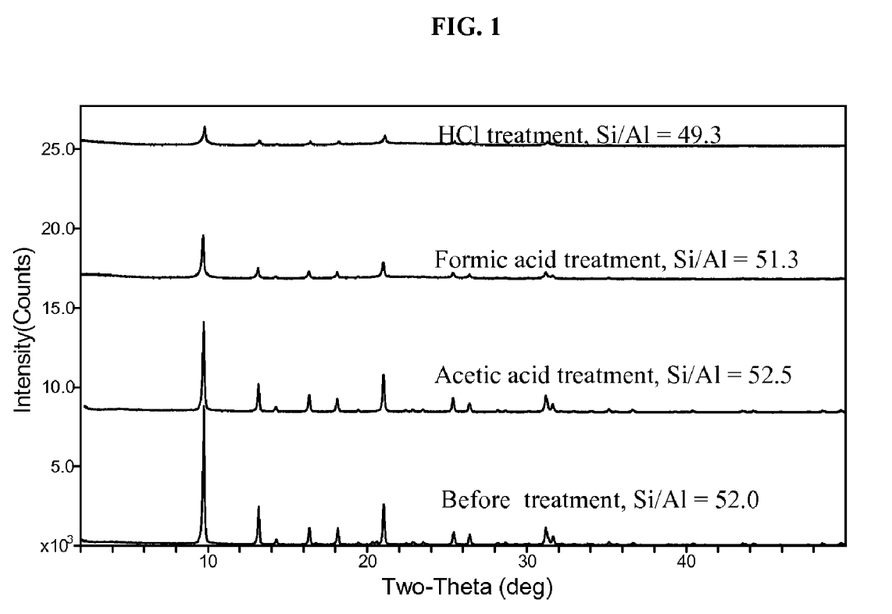
FIG. 1 shows the X-ray diffraction patterns of the CHA-type aluminosilicate molecular sieve of Example 2 in its as-synthesized form and after treatment with acetic acid according to the process of Example 6 and after separate treatments with formic acid and hydrochloric acid according to the process of Example 8.

As with the acetic acid treatment, Si/Al ratio remained essentially unchanged after treatment with both formic acid and HCl. In contrast to acetic acid treatment, however, the treatment with formic acid and hydrochloric acid reduced the XRD diffraction peak intensity significantly, more so with HCl treatment (FIG. 1). This result suggests structural damage with formic acid and HCl. Without wishing to be bound by theory of operation, it is speculated that HCl and formic acid, $HCO_2H$, being smaller than acetic acid, $CH_3CO_2H$, can penetrate the 8-ring pore openings of chabazite, therefore damaging the interior of the chabazite crystals.

Treatment with formic acid and hydrochloric acid also caused selectivity for ethylene and propylene to decrease. This is illustrated in Table 4 below, which provides the results of retesting the product of Example 2 in the MTO process of Example 7 both before treatment and after separate treatment with formic acid and hydrochloric acid.

TABLE 4

| Treatment | Total g MeOH Convn | $C_2^-$ + $C_3^-$ | $C_2=$/$C_3=$ | $C_4^+$ | $CH_4$ | $C_2=$ | $C_2H_6$ | $C_3=$ | $C_3H_8$ | $C_4$'s | $C_5$'s | $C_6+$'s |
|---|---|---|---|---|---|---|---|---|---|---|---|---|
| Untreated | 7.33 | 69.7 | 1.60 | 10.4 | 8.6 | 42.9 | 1.08 | 26.8 | 1.03 | 8.12 | 1.92 | 0.32 |
| $HCO_2H$ | 9.85 | 65.6 | 1.33 | 14.9 | 8.8 | 37.4 | 0.93 | 28.2 | 0.78 | 11.43 | 2.90 | 0.56 |
| HCl | 5.81 | 58.7 | 1.43 | 11.7 | 13.5 | 34.6 | 1.24 | 24.1 | 0.76 | 9.06 | 2.22 | 0.39 |

Example 9

Figure 2:
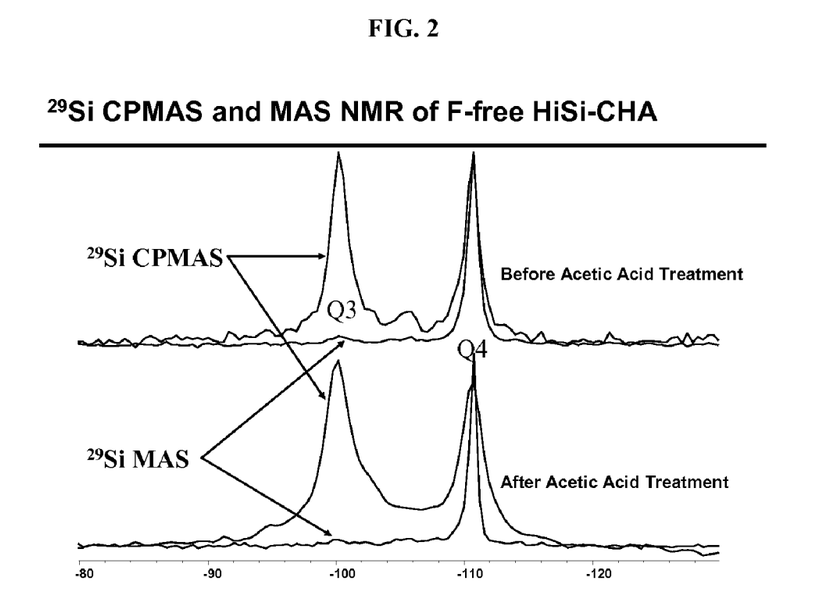
FIG. 2 shows the $^{29}$Si-MAS and $^{29}$Si-CPMAS NMR spectra of the CHA-type aluminosilicate molecular sieve of Example 4 in its as-calcined form and after treatment with acetic acid according to the process of Example 6.

NMR Analysis $^{29}$Si-MAS and $^{29}$Si-CPMAS spectra of the high-silica chabazite samples of Example 4 before and after acetic-acid treatment of Example 6 were taken to monitor the change in the amount of framework defect. The results are shown in FIG. 2 and indicate that there is essentially no change in the amount of framework defect (Q3 signal).

Figure 3:
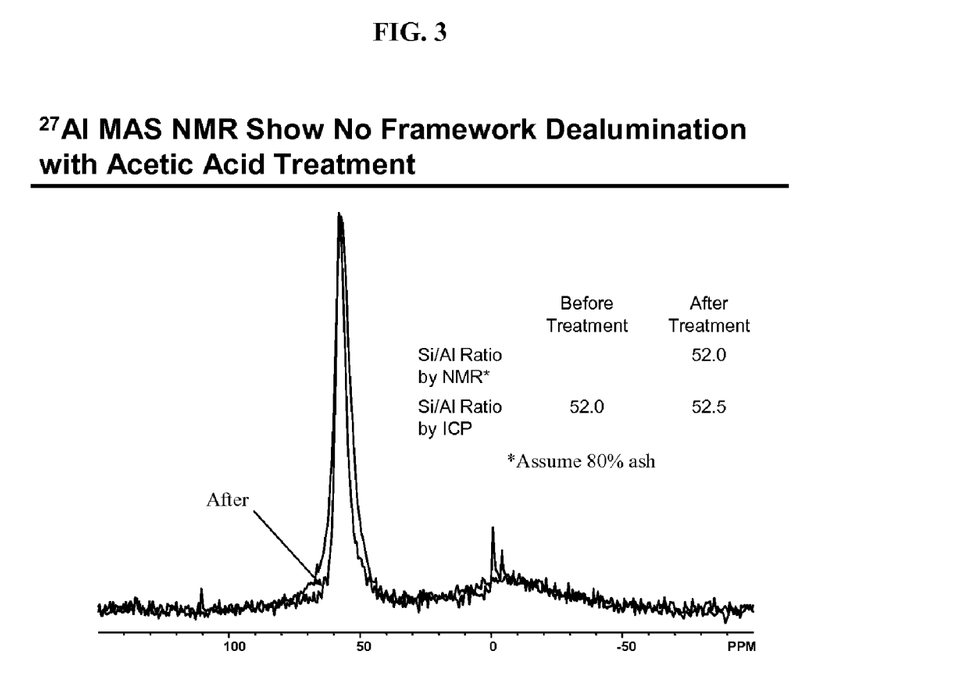
FIG. 3 shows the $^{27}$Al-MAS NMR spectra of the CHA-type aluminosilicate molecular sieve of Example 2 in its as-calcined form and after treatment with acetic acid according to the process of Example 6.

In addition, $^{27}$Al-MAS spectra of the chabazite sample of Example 3 before and after acetic-acid treatment of Example 6 were taken to monitor whether the treatment had caused dealumination. The results are shown in FIG. 3 and indicate only a very weak octahedral Al signal, at near 0 PPM, after the treatment. The framework Al with chemical shift nearing 55 PPM is little changed, indicating that there is essentially no removal of aluminum from the zeolite framework. Quantification of the NMR data shows that the Si/Al ratio remains unchanged after the treatment, consistent with the elemental analysis data.

Figure 4:
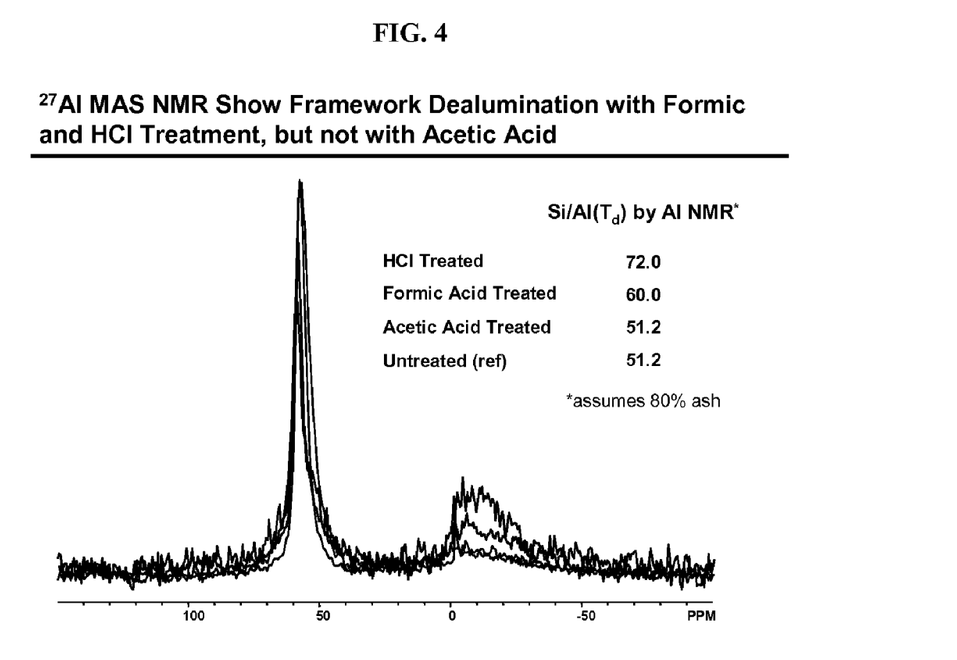
FIG. 4 shows the $^{27}$Al-MAS NMR spectra of the CHA-type aluminosilicate molecular sieve of Example 2 in its as-calcined form and after treatment with acetic acid according to the process of Example 6 and after separate treatments with formic acid and hydrochloric acid according to the process of Example 8.

In contrast to the acetic acid treatment, formic acid and HCl treatment caused a significant reduction in tetrahedral Al (on the framework, signal appearing at about 55 PPM) and a concomitant increase in octahedral Al (non-framework, at between 0 and about −50 PPM), see FIG. 4, even though elemental analysis indicated that there is no loss of Al from the sample (Table 3). Moreover, HCl appears more damaging than formic acid, even though the concentration of the HCl solution is much less than that of the formic acid solution. This trend has been quantified and the Si to tetrahedral Al ratio is shown in FIG. 4. The trend is also consistent with the XRD results shown in FIG. 1.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A method of treating a porous crystalline molecular sieve comprising a CHA framework type material, the method comprising contacting said molecular sieve with acetic acid.

2. The method of claim 1, wherein said treated molecular sieve, when used to convert a methanol-containing feed to olefins, produces less coke by weight of methanol converted as compared with the untreated molecular sieve when used to convert the same methanol-containing feed under identical conditions.

3. The method of claim 1, wherein said contacting is conducted at a temperature of about 50° C. to about 300° C. for a time of about 0.1 hours to about 240 hours.

4. The method of claim 1, wherein said acetic acid employed in said contacting is present as a 0.01 Molar to 10 Molar aqueous solution.

5. The method of claim 1, wherein said molecular sieve has a composition substantially free of framework phosphorus and involving the molar relationship:

$(n)X_2O_3$:$YO_2$, wherein X is a trivalent element, Y is a tetravalent element, and n is non-zero and less than 0.07.

6. The method of claim 5, wherein n is less than 0.02.

7. The method of claim 5, wherein n is less than 0.01.

8. The method of claim 5, wherein Y is silicon, tin, titanium germanium or a combination thereof.

9. The method of claim 5, wherein Y is silicon.

10. The method of claim 5, wherein n is at least 0.0005 and X is aluminum, boron, iron, indium, gallium or a combination thereof.

11. The method of claim 10, wherein X is aluminum.

12. The method of claim 1, wherein the molecular sieve, in its as-synthesized form, is substantially free of fluoride ions.

13. A crystalline material comprising a CHA framework type molecular sieve treated by the method of claim 1.

14. A process for producing olefins comprising contacting an organic oxygenate compound under oxygenate conversion conditions with a catalyst comprising the crystalline material of claim 13.

15. The process of claim 14, wherein said treated CHA framework type molecular sieve produces less coke by weight of organic oxygenate compound converted than the untreated CHA framework type molecular sieve when each is contacted with said organic oxygenate compound under identical oxygenate conversion conditions.

* * * * *